United States Patent [19]

Sombroek et al.

[11] 4,288,452
[45] Sep. 8, 1981

[54] 1-ARYLOXY-3-NITRATOALKYLAMINO-2-PROPANOLS AND USE AS β-RECEPTOR BLOCKER

[75] Inventors: Johannes Sombroek, Darmstadt; Karl-Heinz Becker, Dieburg; Klaus O. Minck, Ober-Ramstadt; Hans-Joachim Enenkel, Darmstadt, all of Fed. Rep. of Germany

[73] Assignee: Merck Patent Gesellschaft mit beschrankter haftung, Darmstadt, Fed. Rep. of Germany

[21] Appl. No.: 10,781

[22] Filed: Feb. 9, 1979

[30] Foreign Application Priority Data

Feb. 9, 1978 [DE] Fed. Rep. of Germany ....... 2805404

[51] Int. Cl.³ ..................... A61K 31/21; A61K 31/47; A61K 31/275; C07C 77/02
[52] U.S. Cl. .................. 424/304; 260/465 E; 260/466; 424/258; 424/262; 424/298; 546/158
[58] Field of Search .......................... 260/465 E, 466; 546/158; 424/258, 262, 298, 304

[56] References Cited

U.S. PATENT DOCUMENTS

| | | | |
|---|---|---|---|
| 3,251,739 | 5/1966 | Peterson | 424/298 |
| 3,644,469 | 2/1972 | Koppe | 260/465 E |
| 3,723,524 | 3/1973 | Augstein | 260/465 E |
| 3,911,136 | 10/1975 | Ferrari | 424/298 |
| 3,925,446 | 12/1975 | Koppe | 260/465 E |
| 3,949,088 | 4/1976 | Samuelsson | 260/465 E |
| 4,083,992 | 4/1978 | Smith | 260/465 E |
| 4,167,581 | 9/1979 | Smith | 424/304 |

FOREIGN PATENT DOCUMENTS 300197 9/1954 Switzerland ................. 260/466

*Primary Examiner*—Anna P. Fagelson
*Attorney, Agent, or Firm*—Millen & White

[57] ABSTRACT

Compounds of the formula

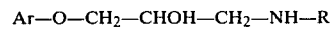

$$Ar-O-CH_2-CHOH-CH_2-NH-R$$

wherein
Ar is phenyl; phenyl monosubstituted or polysubstituted by halogen, cyano, acylamino (in which the acyl group has 1-7 carbon atoms), alkanoyl of 1-4 carbon atoms, alkyl (in which the chain can be interrupted by 1 or 2 oxygen atoms or by one sulfur atom and/or in which a multiple bond can be present) of a total of 1-10 carbon atoms, cycloalkyl of 3-8 carbon atoms, and/or cycloalkoxy of 3-8 carbon atoms; naphthyl; indanyl; indenyl; tetralyl; indolyl; indolyl monosubstituted or polysubstituted by alkyl, each of 1-4 carbon atoms; carbazolyl; or 1,2,3,4-tetrahydro-2-oxoquinolyl; and
R is nitratoalkyl of 2-10 carbon atoms,
and the physiologically acceptable acid addition salts thereof have valuable pharmacological properties, e.g., which make them useful for prophylaxis and treatment of heart problems, e.g., as β-receptor blockers.

6 Claims, No Drawings

1-ARYLOXY-3-NITRATOALKYLAMINO-2-PROPANOLS AND USE AS β-RECEPTOR BLOCKER

The present invention relates to new aryloxyaminopropanols having useful pharmacological properties.

SUMMARY OF THE INVENTION

It is an object of this invention to provide new compounds having valuable properties, especially those which can be used for the preparation of medicaments.

Upon further study of the specification and appended claims, further objects and advantages of this invention will become apparent to those skilled in the art.

These objects have been met by providing novel 1-aryloxy-3-nitratoalkylamino-2-propanols of formula I

$$Ar-O-CH_2CHOH-CH_2-NH-R \quad (I)$$

wherein

Ar is phenyl; phenyl monosubstituted or polysubstituted by halogen, cyano, acylamino (in which the acyl group has 1-7 carbon atoms), alkanoyl of 1-4 carbon atoms, alkyl (in which the chain can be interrupted by 1 or 2 oxygen atoms or by one sulfur atom and/or in which a multiple bond can be present) of a total of 1-10 carbon atoms, cycloalkyl of 3-8 carbon atoms and/or cycloalkoxy of 3-8 carbon atoms; naphthyl; indanyl; indenyl; tetralyl i.e., 1,2,3, or 4-tetrahydronaphthyl; indolyl; indolyl monosubstituted or polysubstituted by alkyl, each of 1-4 carbon atoms; carbazolyl; or 1,2,3,4-tetrahydro-2-oxoquinolyl; and R is nitratoalkyl of 2-10 carbon atoms, and the physiologically acceptable acid addition salts thereof.

DETAILED DISCUSSION

The radical Ar can be, for example, an unsubstituted or substituted phenyl group. For the latter, the phenyl group is preferably monosubstituted (especially in the o-position, also in the p-position but also in the m-position) or disubstituted (especially in the 2,5-positions, but also, for example, in the 2,3-, 2,4-, 3,4- or 3,5-positions). However, it can also be trisubstituted (especially in the 3,4,5-positions, but also, for example, in the 2,3,4-, 2,3,5-, or 2,4,5-positions), tetrasubstituted (for example in the 2,3,4,5-positions) or pentasubstituted. Suitable substituents on the phenyl group include, in particular: (a) F, Cl, Br or I; (b) CN; (c) acylamino, preferably alkanoylamino of 1-7 and preferably 1-4 carbon atoms, such as formylamino or acetylamino and also propionylamino, butyrylamino, isobutyrylamino, valerylamino, caproylamino or heptanoylamino; and also aroylamino, such as benzoylamino; (d) alkanoyl of 1-7 and preferably 1-4 carbon atoms, preferably formyl, acetyl or propionyl and also, for example, butyryl, isobutyryl, valeryl, caproyl or heptanoyl; (e) alkyl of 1-10, and preferably 1-4 carbon atoms, preferably methyl or ethyl, and also, for example, n-propyl, isopropyl, n-butyl, isobutyl, sec-butyl, tert-butyl, pentyl, such as n-pentyl, hexyl, such as n-hexyl, heptyl, such as n-heptyl, octyl, such as n-octyl, nonyl, such as n-nonyl, or decyl, such as n-decyl; alkoxy of 1-10 and preferably 1-4 carbon atoms, preferably methoxy or ethoxy and also, for example n-propoxy, isopropoxy, n-butoxy, isobutoxy, sec-butoxy, tert-butoxy, pentyloxy, hexyloxy, heptyloxy, octyloxy,, nonyloxy or decyloxy; alkoxyalkyl of up to 10 and preferably 2-6 carbon atoms, for example, alkoxymethyl, such as methoxymethyl, alkoxyethyl, such as 1- or 2-methoxyethyl, 1- or 2-n-butoxyethyl or 1- or 2-n-octyloxyethyl; alkoxyalkoxyalkyl of up to 10 and preferably 4-7 carbon atoms, for example alkoxyalkoxymethyl, such as 2-methoxyethoxy-methyl, 2-ethoxyethoxy-methyl or 2-isopropoxyethoxy-methyl, alkoxyalkoxy-ethyl, such as 2-(2-methoxyethoxy)-ethyl or 2-(2-ethoxyethoxy)-ethyl; alkoxyalkoxy of up to 10 and preferably 3-6 carbon atoms, for example, 2-methoxyethoxy, 2-ethoxyethoxy or 2-n-butoxyethoxy; alkylthio of 1-10 and preferably 1-4 carbon atoms, preferably methylthio or ethylthio, and also, for example, n-propylthio, isopropylthio, n-butylthio,, isobutylthio, sec-butylthio, tert-butylthio, pentylthio, hexylthio, hepthythio, octylthio, nonylthio or decylthio; alkylthioalkyl of up to 10 and preferably 2-6 carbon atoms, for example, methylthiomethyl, 2-methylthioethyl or 2-n-butylthioethyl; alkenyl of up to 10 and preferably 2-4 carbon atoms, for example, vinyl, allyl, propenyl, isopropenyl, butenyl, such as 1-buten-1-, -2-, -3-, or -4-yl, 2-buten-1-yl or 2-buten-2-yl, pentenyl, hexenyl or decenyl; alkenyloxy of up to 10 and preferably 2-4 carbon atoms, preferably allyloxy, and also, for example, vinyloxy, propenyloxy, isopropenyloxy, butenyloxy, such as 1-buten-1-, -2-, -3-, or -4-yloxy, 2-buten-1-yloxy or 2-buten-2-yloxy, pentenyloxy, hexenyloxy or decenyloxy; alkenyloxyalkyl of up to 10 and preferably 3-6 carbon atoms, for example allyloxymethyl; alkynyl of up to 10 and preferably 2-4 carbon atoms, for example, ethynyl, 1-propyn-1-yl, propargyl, butynyl, such as 2-butyn-1-yl, pentynyl or decynyl; alkynyloxy of up to 10 and preferably 2-4 carbon atoms, preferably propargyloxy and also, for example, ethynyloxy, 1-propyn-1-yloxy, butynyloxy, such as 2-butyn-1-yloxy, pentynyloxy or decynyloxy; alkynyloxyalkyl of up to 10 and preferably 3-6 carbon atoms, for example, ethynyloxymethyl, propargyloxymethyl or 2-(2-butyn-1-yloxy)-ethyl; (f) cycloalkyl of 3-8 and preferably 5 or 6 carbon atoms, preferably cyclopentyl or cyclohexyl, and also, for example cyclopropyl, cyclobutyl, 1-, 2- or 3-methylcyclopentyl, 1-, 2-, 3- or 4-methylcyclohexyl, cycloheptyl or cyclooctyl; and (g) cycloalkoxy of 3-8 and preferably 5 or 6 carbon atoms, preferably cyclopentyloxy or cyclohexyloxy, and also, for example, cyclopropyloxy, cyclobutyloxy, 1-, 2- or 3-methylcyclopentyloxy, 1-, 2-, 3- or 4-methylcyclohexyloxy, cycloheptyloxy or cyclooctyloxy. As can be seen from the foregoing listing of possible substituents, the phrase "alkyl interrupted by X" is meant to also include alkyl attached to Ar by X.

The radical Ar can also be, for example: 1- or 2-naphthyl; 1-, 2-, 3-, (preferably) 4-, 5-, 6-, or 7-indanyl; 1-, 2-, 3-, (preferably) 4-, 5-, 6- or 7-indenyl; 1-, 2-, 3-, 4-, (preferably) 5-, 6-, 7- or 8-tetralyl; (preferably) 4-, 5-, 6- or 7-indolyl; alkylindolyl, preferably methylindolyl, for example, 2-methyl-4-indolyl or 3-methyl-4-indolyl, and also, for example, 2-ethyl-4-indolyl or 3-ethyl-4-indolyl; dialkylindolyl, preferably dimethylindolyl, for example, 2,3-dimethyl-4-indolyl, and also, for example, 2-methyl-3-ethyl-4-indolyl, 2-ethyl-3-methyl-4-indolyl or 2,3-diethyl-4-indolyl; 1-, 2-, 3- or (preferably) 4-carbazolyl; or 1,2,3,4-tetrahydro-2-oxo-3-, -4-, (preferably)-5-, -6-, -7- or -8-quinolyl.

Preferred individual radicals Ar include, for example, phenyl; halogenophenyl, such as o-, m- or p-fluorophenyl, o-, m- or p-chlorophenyl, o-, m- or p-bromophenyl or o-, m- or p-iodophenyl; dihalogenophenyl, such as 2,3-, 2,4-, 2,5-, 3,4- or 3,5-dichlorophenyl; o-, m- or p-cyanophenyl; o-, m- or p-acetylaminophenyl; 2-acetyl-4-butyrylaminophenyl; o-, m- or p-tolyl, o-, m- or p-ethylphenyl, o-, m- or p-isopropylphenyl or 2,3-, 2,4-, 2,5-, 3,4- or 3,5-dimethylphenyl; 2-chloro-5-methylphenyl or 2-methyl-5-chlorophenyl; o-, m- or p-methoxyphenyl, o-, m- or p-ethoxyphenyl, o-, m- or p-2-methoxyethylphenyl, o-, m- or p-(2-isopropoxyethoxymethyl)-phenyl, o-, m- or p-allylphenyl, o-, m- or p-allyloxyphenyl, o-, m- or p-propargyloxyphenyl or o-, m- or p-methylthiophenyl; o-, m- or p-cyclopropylphenyl; o-, m- or p-cyclopentylphenyl; o-, m- or p-cyclohexylphenyl; 1-naphthyl; 4-indanyl; 4-indenyl; 5-tetralyl; 4-indolyl or 2-methyl-4-indolyl; 2,3-dimethyl-4-indolyl; 4-carbazolyl and 1,2,3,4-tetrahydro-2-oxo-5-quinolyl.

The radical R is a straight-chain or (preferably) branched nitratoalkyl group of 2-10 and preferably 2-6 carbon atoms. Particularly preferred as R is the group $-CZ^1Z^2-(CH_2)_m-CZ^3Z^4-O-NO_2$, in which $Z^1$ to $Z^4$ are each H or $CH_3$ and m is 0-2. Individual preferred radicals R include $-CH_2CH_2-O-NO_2$, $-CH(CH_3)-CH_2-O-NO_2$, $-C(CH_3)_2-CH_2-O-NO_2$, $-CH(CH_3)-CH(CH_3)-O-NO_2$, $-CH_2-CH(CH_3)-O-NO_2$, $-CH_2-C(CH_3)_2-O-NO_2$, $-CH_2CH_2CH_2-O-NO_2$, $-CH(CH_3)-CH_2CH_2-O-NO_2$, $-C(CH_3)_2-CH_2CH_2-O-NO_2$, $-C(CH_3)_2-CH_2-CH(CH_3)-O-NO_2$, $-C(CH_3)_2-CH_2-C(CH_3)_2-O-NO_2$, $-CH(C_2H_5)-CH_2CH_2-O-NO_2$, $-C(CH_3)(C_2H_5)-CH_2CH_2-O-NO_2$, $-C(C_2H_5)_2-CH_2CH_2-ONO_2$, $-CH(CH_3)-CH_2CH_2CH_2-O-NO_2$ and $-C(CH_3)_2-CH_2CH_2CH_2-O-NO_2$. In particular, the following radicals R are preferred: 1-methyl-3-nitratopropyl, 1,1-dimethyl-3-nitratopropyl and also 1,1,3-trimethyl-3-nitratopropyl, 1-methyl-4-nitratobutyl and 1,1-dimethyl-4-nitratobutyl.

Accordingly, the present invention relates in particular to those compounds of formula I in which at least one of the radicals Ar and R has one of the preferred meanings indicated above.

Some preferred groups of compounds can be expressed by the following partial formulae Ia to If, which correspond to formula I and in which the radicals not defined in more detail are as defined for formula I, and in which in Ia Ar is phenyl, chlorophenyl, dichlorophenyl, chloromethyl-phenyl, cyanophenyl, acetylaminophenyl, tolyl, dimethylphenyl, isopropylphenyl, methoxyphenyl, allylphenyl, allyloxyphenyl, 2-methoxyethylphenyl, 2-isopropoxyethoxymethylphenyl, methylthiophenyl, cyclopropylphenyl, cyclopentylphenyl, cyclohexylphenyl, naphthyl, indenyl, indolyl, carbazolyl or 1,2,3,4-tetrahydro-2-oxoquinolyl;

in Ib Ar is phenyl, 2,5-dichlorophenyl, 2-chloro-5-methylphenyl, o-cyanophenyl, p-acetylaminophenyl, 2,3-dimethylphenyl, o-isopropylphenyl, o-methoxyphenyl, o-allylphenyl, o-allyloxyphenyl, p-2-isopropoxyethoxymethyl-phenyl, o-methylthiophenyl, o-cyclohexylphenyl, 1-naphthyl, 4-indenyl, 4-indolyl, 4-carbazolyl or 1,2,3,4-tetrahydro-2-oxo-5-quinolyl;

in Ic Ar is o-cyanophenyl, o-isopropylphenyl, o-methoxyphenyl, o-allyloxyphenyl, 1-naphthyl, 4-indenyl, 4-indolyl or 4-carbazolyl;

in Id R is 1-methyl-3-nitratopropyl, 1,1-dimethyl-3-nitratopropyl, 1,1,3-trimethyl-3-nitratopropyl, 1-methyl-4-nitratobutyl or 1,1-dimethyl-4-nitratobutyl;

in Ie Ar is o-cyanophenyl, 1-isopropylphenyl, o-methoxyphenyl, o-allyloxyphenyl, 1-naphthyl, 4-indenyl, 4-indolyl or 4-carbazolyl and R is 1-methyl-3-nitratopropyl, 1,1-dimethyl-3-nitratopropyl, 1,1,3-trimethyl-3-nitratopropyl, 1-methyl-4-nitratobutyl or 1,1-dimethyl-4-nitratobutyl; and in If Ar is o-cyanophenyl, o-isopropylphenyl, o-methoxyphenyl, o-allyloxyphenyl, 1-naphthyl, 4-indenyl, 4-indolyl or 4-carbazolyl and R is 1-methyl-3-nitratopropyl or 1,1-dimethyl-3-nitratopropyl.

The compounds of the formula I possess at least one asymmetric carbon atom and can contain additional asymmetric carbon atoms in the substituents Ar and R. They can therefore be in the form of racemates or in an optically active form. As a rule, they are synthesized in the form of racemates.

The present invention also relates to a process for preparing 1-aryloxy-3-nitratoalkylamino-2-propanols of formula I and of their physiologically acceptable acid addition salts, which comprises (a) reacting a compound of formula II $$Ar-O-CH_2-CHQ-CH_2Y \quad (II)$$

with a compound of formula III $$Z-R \quad (III)$$

in which one of the radicals Y and Z is $NH_2$ and the other is X, Q is OH or together with X is an oxygen atom, X is Hal, OH, a functionally modified OH group or (in II) together with Q is an oxygen atom and Hal is Cl, Br or I and Ar and R are as defined above; or (b) reacting a phenol of formula IV $$Ar-OH \quad (IV)$$

in which Ar is as defined above, with a nitratoalkylamine of formula V $$X-CH_2-CHQ-CH_2-NH-R \quad (V)$$

in which R, Q and X are as defined above; or (c) treating with a solvolyzing agent, a compound which corresponds to formula I but which additionally carries one or more solvolytically detachable groups in place of one or more H atoms; or (d) esterifying a compound of formula VI $$Ar-O-CH_2-CHOH-CH_2-NH-E \quad (VI)$$

in which E is a hydroxyalkyl group with 2-10 carbon atoms and Ar is as defined above, or one of its reactive derivatives, with nitric acid or one of its reactive derivatives or (e) optionally converting a base of the formula I resulting from one of these processes by treatment with an acid into one of its physiologically acceptable acid addition salts.

The radical X can be present in the starting materials of the formulae II, III and V. This radical is preferably Cl or Br, and also I, OH or a functionally modified OH group. Herein, functionally modified OH groups are understood to mean, in particular, reactively esterified OH groups, for example, alkylsulphonyloxy of preferably 1-6 carbon atoms, such as methanesulphonyloxy, or arylsulphonyloxy of preferably 6-10 carbon atoms, such as benzenesulphonyloxy, p-toluenesulphonyloxy or 1- or 2-naphthalene-sulphonyloxy.

In other respects, the compounds of formula I are prepared according to methods which are in themselves known, such as are described in the literature (for example in the standard works, such as Houben-Weyl, Methoden der Organischen Chemie (Methods of Organic Chemistry), Georg-Thieme-Verlag, Stuttgart; Organic Reactions, John Wiley and Sons, Inc., New York), and specifically under conditions which are known and suitable for the said reactions. It is also possible to utilize variants which are in themselves known and are not mentioned in more detail herein.

Some of the starting materials for the preparation of the compounds of formula I are known and some are new. The new starting materials can be prepared according to processes which are in themselves known, as a rule analogously to the known starting materials.

The starting materials can, if desired, also be formed in situ, in that they are not isolated from the reaction mixture but are immediately reacted further to give the compounds of formula I.

In the text which follows, the radicals Ar, E, Hal, Q, R, X, Y and Z have the meanings defined for formulae I to V unless expressly stated otherwise.

Individually, the starting materials of the formula II are as a rule known. They are obtainable, for example, by reacting the phenols of the formula Ar—OH (IV) with compounds of the formula X—CH$_2$—CHQ—CH$_2$Y (for example epichlorohydrin or epibromohydrin). Primary amines of the formula II (Y=NH$_2$) can be prepared, for example, by reacting epoxides of formula II (Q and Y together are an oxygen atom) with ammonia or with benzylamine and subsequently removing the benzyl group hydrogenolytically.

Some of the starting materials of formula III are known and some are new. The amines of formula III (Z=NH$_2$) can be obtained by esterification of the corresponding aminoalkanols of the formula H$_2$N—E with nitric acid or can be obtained from the corresponding halogen compounds of formula III (Z=Hal) by reaction with ammonia. Compounds of formulae II and III in which the radicals Y or Z are functionally modified OH groups are accessible by functional modification of the corresponding alcohols, for example, by reaction with alkyl- or aryl-sulphonyl halides in the presence of pyridine.

The phenols of formula IV are as a rule known. They can be obtained by conventional phenol syntheses. Nitratoalkylamines of formula V can, for example, be prepared by reacting compounds of the formula X—CH$_2$—CHQ—CH$_2$Y (preferably epoxides such as epichlorohydrin) with amines of formula III (Z=NH$_2$).

The compounds of formula I are preferably prepared by reacting the compounds of formula II with the compounds of formula III. On the other hand, epoxides of formula II (Q and Y together are an oxygen atom), halogenoalcohols of formula II (Q=OH, Y=Hal) or diols or their functional derivatives of formula II (Q=OH, Y=OH or functionally modified OH) can be reacted with amines of formula III (Z=NH$_2$); on the other hand, amines of formula II (Q=OH, Y=NH$_2$) can be reacted with compounds of formula III (Z=X). The reaction of the mentioned epoxides with amines of formula R—NH$_2$ is preferred.

The reaction of the compounds of formula II with the compounds of formula III proceeds in the presence or in the absence of an additional inert solvent at temperatures between about 0 and 150 and preferably between about 20 and 80. Suitable inert solvents are those which are known from the literature for aminations of this type, for example, water, alcohols, such as methanol, ethanol, isopropanol or n-butanol; ethers, such as diethyl ether, diisopropyl ether, tetrahydrofuran or dioxane; hydrocarbons, such as benzene, toluene or xylene; halogenated hydrocarbons, such as methylene chloride, chloroform or trichloroethylene; nitriles, such as acetonitrile; amides, such as dimethylformamide; and sulphoxides, such as dimethylsulphoxide. Mixtures of these solvents can also be used. The amines are preferably used at least in a molar ratio of 1:1 or in excess.

It is also possible to add an additional base, for example, an inorganic base such as sodium hydroxide or potassium hydroxide, sodium carbonate, potassium carbonate, sodium bicarbonate or potassium bicarbonate. If the starting compounds have a structure such that 1 mole of acid is split off during the reaction (for example, halogenohydrins, so that hydrogen halide is split off), it is preferred to use either an additional base or an excess of the amine.

If X is OH, or also an alkyl- or aryl-sulphonyloxy group, it can be advisable also to add an acid catalyst, for example, an inorganic acid (such as sulphuric acid, polyphosphoric acid, hydrobromic acid or hydrochloric acid) and/or an organic acid (such as formic acid, acetic acid, propionic acid or p-toluenesulphonic acid). An excess of the acid can at the same time also serve as the solvent.

The reaction times required are between about 10 minutes and 7 days, depending on the starting materials used and on the reaction temperature. The reaction can also be carried out under pressure (of up to about 200 atmospheres) and can be accelerated in this way.

The compounds of formula I can also be obtained by reacting the phenols of formula IV with the nitratoalkylamines of formula V. For example, the phenol IV can first be converted into a salt, especially a metal salt, for example, an alkali metal salt (Li, Na or K salt). The phenol can be reacted with a metal salt-forming reagent, for example, an alkali metal (for example Na), an alkali metal hydride or alkali metal amide (for example, LiH or NaH, NaNH$_2$ or KNH$_2$), an alkali metal alcoholate (in which the alcohol portion preferably has 1–4 carbon atoms, for example, lithium methylate, ethylate or tert-butylate, sodium methylate, ethylate or tert-butylate or potassium methylate, ethylate or tert-butylate), an organometallic compound (for example, butyl-lithium, phenyl-lithium or phenylsodium) or a hydroxide, carbonate or bicarbonate of a metal (for example of Li, Na, K or Ca). The preparation of the phenolate is advantageously carried out in the presence of a solvent or solvent mixture. Suitable solvents include, for example, hydrocarbons (such as hexane, benzene, toluene or xylene), ethers (for example, diethyl ether, diisopropyl ether, tetrahydrofuran, dioxane or diethylene glycol dimethyl ether), amides (for example, dimethylformamide), alcohols (for example, methanol or ethanol) or ketones (for example, acetone or butanone).

The phenol IV or its salt is preferably reacted with the compound V is the presence of a diluent, for example, that solvent which has been used for the preparation of the salt; however, this solvent can be replaced by another solvent or can be diluted with another solvent. As a rule, the reaction is carried out at temperature between about −20° and 150° and preferably between 20° and 80°.

The phenolate can also be formed in situ. In this case, the phenol IV and the compound V are allowed to react with one another in the presence of a base. A particularly preferred method comprises heating the compounds IV and V together with an alcoholic-aqueous solution of sodium hydroxide for about 5 to 15 hours.

The phenoxy-amino-propanols of formula I are also obtainable by solvolysis of a compound which corresponds to formula I but which additionally carries one or more solvolytically detachable groups in place of one or more H atoms.

Suitable starting materials for this process variant are, in particular, compounds of formula Ar—O—CH$_2$—CHOR$^3$—CH$_2$—NR—R$^4$ (VII), in which the radical R$^3$ is H or a hydroxyl protective group and the radical R$^4$ is H or an amino protective group, but the radicals R$^3$ and R$^4$ cannot at the same time be H, and Ar and R are as defined above.

The terms "hydroxyl protective group" and "amino protective group" are generally known and relate to groups which are suitable for protecting (or blocking) a hydroxyl group or an amino group against chemical reactions but which are easily removable after the desired chemical reaction has been carried out at other positions in the molecule. Since these protective groups are removed according to this process variant of this invention, their nature and size is in other respects not critical. Preferably, R$^3$ and/or R$^4$ are, however, acyl of 1–20 and especially 1–8 carbon atoms (for example, alkanoyl, such as acetyl, aroyl, such as benzoyl, aralkanoyl, such as phenylacetyl, alkoxycarbonyl, such as methoxycarbonyl, aralkoxycarbonyl, such as benzyloxycarbonyl, arylsulphonyl, such as p-toluenesulphonyl, or optionally substituted benzyl (for example, benzyl, p-nitrobenzyl or triphenylmethyl)).

Solvolysis of these compounds preferably takes place by the action of a solvent, such as water (hydrolysis) or of an alcohol with preferably 1–4 carbon atoms (alcoholysis) in the presence of an acid or basic catalyst, for example, a mineral acid, such as sulphuric acid or hydrochloric acid, a metal hydroxide, such as sodium hydroxide, potassium hydroxide, calcium hydroxide, barium hydroxide, lead hydroxide or silver hydroxide, or a metal salt or ammonium salt, such as sodium carbonate or potassium carbonate or ammonium chloride. The alcohols used are preferalby methanol, ethanol or isopropanol; mixtures of water with one of these alcohols can also be used. The solvolysis is preferably carried out at temperatures between about 0° and about 80°.

The nitrato esters of the formula I are also obtainable by partial esterification of corresponding diols of the formula VI or of their reactive derivatives (for example, their chlorine, bromine or iodine derivatives; corresponding to VI except that chloro-, bromo- or iodoalkyl is in place of E) with nitric acid or one of its reactive derivatives, for example, one of its salts, especially the silver salt or mercury-I salt. The esterification is carried out, for example, in the presence of an inert solvent, for example, of an ether, such as tetrahydrofuran or 1,2-dimethoxyethane, or in the presence of acetic anhydride, at temperatures between about 20° and 80°.

A base of the formula I can be converted, using an acid, into the corresponding acid addition salt. Acids which can be used for this reaction are those which give physiologically acceptable salts. Thus, it is possible to use inorganic acids, for example, sulphuric acid, nitric acid, hydrogen halide acids, such as hydrochloric acid or hydrobromic acid, or phosphoric acids, such as orthophosphoric acid, and also organic acids, especially aliphatic, alicyclic, araliphatic, aromatic or heterocyclic monobasic or polybasic carboxylic or sulphonic acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenyl-propionic acid, citric acid, gluconic acid, ascorbic acid, nicotinic acid, isonicotinic acid, methane- or ethane-sulphonic acid, ethanedisulphonic acid, 2-hydroxyethanesulphonic acid, benzenesulphonic acid, p-toluenesulphonic acid or naphthalene-mono- and -disulphonic acids. The free bases of formula I can, if desired, be liberated from their salts by treatment with strong bases, such as sodium hydroxide or potassium hydroxide, sodium carbonate or potassium carbonate.

The compounds of formula I are usually in the form of racemates. If the compounds have two or more centers of asymmetry, they are generally obtained from their synthesis in the form of mixtures of racemates, from which the individual racemates can be isolated, for example, by repeated recrystallization from suitable solvents, and obtained in a pure form.

Resulting racemates can be resolved into their optical antipodes by methods which are in themselves known, by mechanical or chemical routes. Preferably, diastereomers are formed from the racemic mixture by reaction with an optically active resolving agent. Suitable resolving agents are, for example, optically active acids, such as the D and L forms of tartaric acid, dibenzoyltartaric acid, diacetyltartaric acid, β-camphorsulphonic acid, mandelic acid, malic acid or lactic acid.

Furthermore, it is possible to obtain optically active compounds by the methods described above by using starting materials which are already optically active.

It has been found that the compounds of formula I possess very valuable pharmacological properties and are well tolerated. In particular, they block the adrenergic β-receptors and display isoprenaline-antagonistic actions on the heart rate, for example, of guinea pigs, cats or dogs, which are detectable, for example, by the method which is described in more detail in German Auslegeschrift No. 1,493,564. Some of the compounds display a cardioselective action. Moreover, they effect an advantageous peripheral vasodilation. Furthermore, effects which lower the cholesterol level and lower the triglyceride level also arise and these can be determined on rats by the methods described by Levine et al (Automation in Analytical Chemistry, Technicon Symposium, 1967, Mediad, New York, page 25–28) and by Noble and Campbell (Clin. Chem. 16 (1970), pages 166–170). Furthermore, the compounds act on the central nervous system and also have thrombocyte aggregation-inhibiting, antiarrhythmic and lipolysis-inhibiting effects, which likewise can be determined by the methods customary for this purpose. The compound thus have a very broad spectrum of action.

Accordingly, the compounds can be used as medicaments in human medicine and veterinary medicine, especially for the prophylaxis and the treatment of heart, circulatory and vascular diseases, for example, of angina pectoris and cardiac rhythm disorders. Furthermore, they can be used as intermediates for the preparation of other medicinally active ingredients.

Thus, the invention also relates to the use of the compounds of formula I and their physiologically acceptable salts for the preparation of pharmaceutical formulations, especially by a non-chemical route. For this purpose, the compounds can be brought, together with at least one excipient or auxiliary and, if desired, in combination with one or more additional active ingredients, into a suitable dosage form.

Accordingly, the invention also relates to agents, especially pharmaceutical formulations, containing a compound of formula I and/or one of its physiologically acceptable salts.

These formulations can be used as medicaments in human medicine or veterinary medicine. Excipients which can be used are organic or inorganic substances which are suitable for enteral (for example oral) or parenteral administration or topical application and do not react with the new compounds, for example water, vegetable oils, benzyl alcohols, polyethylene glycols, glycerol triacetate, gelatine, carbohydrates such as lactose or starch, magnesium stearate, talc and white petroleum jelly. Formulations for oral administration include in particular tablets, dragees, capsules, syrups, elixirs or drops; for rectal use are suppositories; for parenteral administration are solutions, preferably oily or aqueous solutions, and also suspensions, emulsions or implants; and for topical use are ointments, creams or powders. The new compounds can also be lyophilized and the resulting lyophilizates can be used, for example, to prepare injection preparations. The indicated formulations can be sterilized and/or contain auxiliaries, such as lubricants, preservatives, stabilizers and/or wetting agents, emulsifiers, salts for influencing the osmotic pressure, buffer substances, dyestuffs, flavorings and/or aroma-generating substances. If desired, they can also contain one or more additional active ingredients, for example, one or more vitamins.

The invention also relates to the use of the compounds of the formula I for combating diseases, especially heart, circulatory and vascular diseases, and to their use in the therapeutic treatment of the human or animal body.

The substances according to this invention are as a rule administered analogously to known cardiac preparations and circulatory preparations which are available commercially, especially β-receptor blockers, preferably in dosages between about 0.5 and 100 mg and especially between 2 and 50 mg per dosage unit. The daily dose is preferably between about 0.01 and 2 mg/kg of body weight. The particular dose for each specific patient, i.e., mammals including humans, depends, however, on very diverse factors, for example, on the effectiveness of the particular compound employed; on the age, the body weight, the general state of health and the sex of the patient; on the diet, on the time and routine of administration, on the rate of excretion, on the combination of medicaments and on the severity of the particular disease for which therapy is being given. Oral administration is preferred.

Each of the compounds of formula I named in the examples which follow is particularly suitable for the preparation of pharmaceutical formulations.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

In the examples "customary working up" means: water is added if necessary; the reaction mixture is extracted with an organic solvent, such as ethyl acetate, chloroform or methylene chloride; the organic phase is separated off, dried over sodium sulphate and filtered; the filtrate is evaporated; and the residue is purified by chromatography and/or crystallization (of the base or one of its salts).

EXAMPLE 1

21.3 g of 1,1-dimethyl-3-nitratopropylamine nitrate are dissolved in 200 ml of methanol; 5.4 g of Na methylate and then 24.3 g of 1-chloro-3-o-allyloxyphenoxy-2-propanol are added at 20°, while stirring; and the mixture is warmed at 50° for 18 hours. The reaction mixture is cooled and worked up in the customary manner and gives 1-o-allyloxy-phenoxy-3-(1,1-dimethyl-3-nitratopropylamino)-2-propanol. Hemi-fumarate, m.p. 98°–99°.

EXAMPLES 2 to 146

The following compounds are obtained analogously to Example 1, from the corresponding 1-chloro-3-ArO-2-propanols or 1,2-epoxy-3-ArO-propanes and the corresponding nitratoalkylamines:

2. 1-o-Isopropylphenoxy-3-(2-nitratoethylamino)-2-propanol hemi-fumarate, m.p. 122°–123°.
3. 1-o-Allylphenoxy-3-(2-nitratoethylamino)-2-propanol, hemi-fumarate, m.p. 131°–133°.
4. 1-(1-Naphthyloxy)-3-(2-nitratoethylamino)-2-propanol, hemi-fumarate, m.p. 117°–120°.
5. 1-Phenoxy-3-(1-methyl-3-nitratopropylamino)-2-propanol.
6. 1-o-Chlorophenoxy-3-(1-methyl-3-nitratopropylamino)-2-propanol.
7. 1-(2,5-Dichlorophenoxy)-3-(1-methyl-3-nitratopropylamino)-2-propanol.
8. 1-(2-Methyl-5-chlorophenoxy)-3-(1-methyl-3-nitratopropylamino)-2-propanol.
9. 1-o-Cyanophenoxy-3-(1-methyl-3-nitratopropylamino)-2-propanol, hemi-fumarate, m.p. 131°–133°.
10. 1-p-Cyanophenoxy-3-(1-methyl-3-nitratopropylamino)-2-propanol.
11. 1-p-Formylaminophenoxy-3-(1-methyl-3-nitratopropylamino)-2-propanol.
12. 1-o-Acetylaminophenoxy-3-(1-methyl-3-nitratopropylamino)-2-propanol.
13. 1-p-Acetylaminophenoxy-3-(1-methyl-3-nitratopropylamino)-2-propanol, hemi-fumarate, m.p. 140°–142°.
14. 1-p-Heptanoylaminophenoxy-3-(1-methyl-3-nitratopropylamino)-2-propanol.
15. 1-o-Formylphenoxy-3-(1-methyl-3-nitratopropylamino)-2-propanol.
16. 1-o-Acetylphenoxy-3-(1-methyl-3-nitratopropylamino)-2-propanol.
17. 1-o-Butyrylphenoxy-3-(1-methyl-3-nitratopropylamino)-2-propanol.
18. 1-o-Tolyloxy-3-(1-methyl-3-nitratopropylamino)-2-propanol.
19. 1-m-Tolyloxy-3-(1-methyl-3-nitratopropylamino)-2-propanol.
20. 1-p-Tolyloxy-3-(1-methyl-3-nitratopropylamino)-2-propanol.
21. 1-o-Ethylphenoxy-3-(1-methyl-3-nitratopropylamino)-2-propanol.

22. 1-o-Isopropylphenoxy-3-(1-methyl-3-nitratopropylamino)-2-propanol, hemi-fumarate, m.p. 130°–132°.
23. 1-p-Isopropylphenoxy-3-(1-methyl-3-nitratopropylamino)-2-propanol.
24. 1-(2,3-dimethylphenoxy)-3-(1-methyl-3-nitratopropylamino)-2-propanol, hemi-fumarate, m.p. 152°.
25. 1-o-Methoxyphenoxy-3-(1-methyl-3-nitratopropylamino)-2-propanol, hemi-fumarate, m.p. 127°–128°.
26. 1-p-Methoxyphenoxy-3-(1-methyl-3-nitratopropylamino)-2-propanol.
27. 1-o-Ethoxyphenoxy-3-(1-methyl-3-nitratopropylamino)-2-propanol.
28. 1-(p-2-Methoxyethylphenoxy)-3-(1-methyl-3-nitratopropylamino)-2-propanol.
29. 1-(p-2-Isopropoxyethoxymethylphenoxy)-3-(1-methyl-3-nitratopropylamino)-2-propanol, hemi-fumarate, m.p. 90°–92°.
30. 1-o-Methylthiophenoxy-3-(1-methyl-3-nitratopropylamino)-2-propanol.
31. 1-p-Methylthiophenoxy-3-(1-methyl-3-nitratopropylamino)-2-propanol.
32. 1-o-Vinylphenoxy-3-(1-methyl-3-nitratopropylamino)-2-propanol.
33. 1-o-Allylphenoxy-3-(1-methyl-3-nitratopropylamino)-2-propanol, hemi-fumarate, m.p. 121°–124°.
34. 1-p-Allylphenoxy-3-(1-methyl-3-nitratopropylamino)-2-propanol.
35. 1-o-Allyloxyphenoxy-3-(1-methyl-3nitratopropylamino)-2-propanol, hemi-fumarate, m.p. 100°–102°.
36. 1-p-Allyloxyphenoxy-3-(1-methyl-3-nitratopropylamino)-2-propanol.
37. 1-o-Propargylphenoxy-3-(1-methyl-3-nitratopropylamino)-2-propanol.
38. 1-p-Propargylphenoxy-3-(1-methyl-3-nitratopropylamino)-2-propanol.
39. 1-o-Propargyloxyphenoxy-3-(1-methyl-3-nitratopropylamino)-2-propanol.
40. 1-p-Propargyloxyphenoxy-3-(1-methyl-3-nitratopropylamino)-2-propanol.
41. 1-o-Cyclopropylphenoxy-3-(1-methyl-3-nitratopropylamino)-2-propanol.
42. 1-o-Cyclobutylphenoxy-3-(1-methyl-3-nitratopropylamino)-2-propanol.
43. 1-o-Cyclopentylphenoxy-3-(1-methyl-3-nitratopropylamino)-2-propanol.
44. 1-o-Cyclohexylphenoxy-3-(1-methyl-3-nitratopropylamino)-2-propanol.
45. 1-o-Cycloheptylphenoxy-3-(1-methyl-3-nitratopropylamino)-2-propanol.
46. 1-o-Cyclooctylphenoxy-3-(1-methyl-3-nitratopropylamino)-2-propanol.
47. 1-o-Cyclopropyloxyphenoxy-3-(1-methyl-3-nitratopropylamino)-2-propanol.
48. 1-p-Cyclopropyloxyphenoxy-3-(1-methyl-3-nitratopropylamino)-2-propanol.
49. 1-o-Cyclobutyloxyphenoxy-3-(1-methyl-3-nitratopropylamino)-2-propanol.
50. 1-p-Cyclobutyloxyphenoxy-3-(1-methyl-3-nitratopropylamino)-2-propanol.
51. 1-o-Cyclopentyloxyphenoxy-3-(1-methyl-3-nitratopropylamino)-2-propanol.
52. 1-p-Cyclopentyloxyphenoxy-3-(1-methyl-3-nitratopropylamino)-2-propanol.
53. 1-o-Cyclohexyloxyphenoxy-3-(1-methyl-3-nitratopropylamino)-2-propanol.
54. 1-p-Cyclohexyloxyphenoxy-3-(1-methyl-3-nitratopropylamino)-2-propanol.
55. 1-o-Cycloheptyloxyphenoxy-3-(1-methyl-3-nitratopropylamino)-2-propanol.
56. 1-o-Cyclooctyloxyphenoxy-3-(1-methyl-3-nitratopropylamino)-2-propanol.
57. 1-(1-Naphthyloxy)-3-(1-methyl-3-nitratopropylamino)-2-propanol, hemi-fumarate, m.p. 155°–157°.
58. 1-(4-Indanyloxy)-3-(1-methyl-3-nitratopropylamino)-2-propanol.
59. 1-(4-Indenyloxy)-3-(1-methyl-3-nitratopropylamino)-2-propanol.
60. 1-(5-Tetralyloxy)-3-(1-methyl-3-nitratopropylamino)-2-propanol.
61. 1-(4-Indolyloxy)-3-(1-methyl-3-nitratopropylamino)-2-propanol, m.p. 57°–60°.
62. 1-(2-Methyl-4-indolyloxy)-3-(1-methyl-3-nitratopropylamino)-2-propanol.
63. 1-(2,3-Dimethyl-4-indolyloxy)-3-(1-methyl-3-nitratopropylamino)-2-propanol.
64. 1-(4-Carbazolyloxy)-3-(1-methyl-3-nitratopropylamino)-2-propanol, m.p. 111°–113°.
65. 1-(1,2,3,4-Tetrahydro-2-oxo-5-quinolyloxy)-3-(1-methyl-3-nitratopropylamino)-2-propanol.
66. 1-Phenoxy-3-(1,1-dimethyl-3-nitratopropylamino)-3-propanol, hemi-fumarate, m.p. 128°.
67. 1-o-Chlorophenoxy-3(1,1-dimethyl-3-nitratopropylamino)-2-propanol.
68. 1-(2,5-Dichlorophenoxy)-3-(1,1-dimethyl-3-nitratopropylamino)-2-propanol.
69. 1-(2-Methyl-5-chlorophenoxy)-3-(1,1-dimethyl-3-nitratopropylamino)-2-propanol, hemi-fumarate, m.p. 131°–132°.
70. 1-o-Cyanophenoxy-3-(1,1-dimethyl-3-nitratopropylamino)-2-propanol, hemi-fumarate, m.p. 91°–94°.
71. 1-p-Cyanophenoxy-3-(1,1-dimethyl-3-nitratopropylamino)-2-propanol.
72. 1-p-Formylaminophenoxy-3-(1,1-dimethyl-3-nitratopropylamino)-2-propanol.
73. 1-o-Acetylaminophenoxy-3-(1,1-dimethyl-3-nitratopropylamino)-2-propanol.
74. 1-p-Acetylaminophenoxy-3-(1,1-dimethyl-3-nitratopropylamino)-2-propanol.
75. 1-p-Heptanoylaminophenoxy-3-(1,1-dimethyl-3-nitratopropylamino)-2-propanol.
76. 1-o-Formylphenoxy-3-(1,1-dimethyl-3-nitratopropylamino)-2-propanol.
77. 1-o-Acetylphenoxy-3-(1,1-dimethyl-3-nitratopropylamino)-2-propanol.
78. 1-o-Butyrylphenoxy-3-(1,1-dimethyl-3-nitratopropylamino)-2-propanol.
79. 1-o-Tolyloxy-3-(1,1-dimethyl-3-nitratopropylamino)-2-propanol.
80. 1-m-Tolyloxy-3-(1,1-dimethyl-3-nitratopropylamino)-2-propanol.
81. 1-p-Tolyloxy-3-(1,1-dimethyl-3-nitratopropylamino)-2-propanol.
82. 1-o-Ethylphenoxy-3-(1,1-dimethyl-3-nitratopropylamino)-2-propanol.
83. 1-o-Isopropylphenoxy-3-(1,1-dimethyl-3-nitratopropylamino)-2-propanol, hemi-fumarate, m.p. 128°.
84. 1-p-Isopropylphenoxy-3-(1,1-dimethyl-3-nitratopropylamino)-2-propanol.

85. 1-(2,3-Dimethylphenoxy)-3-(1,1-dimethyl-3-nitratopropylamino)-2-propanol.
86. 1-o-Methoxyphenoxy-3-(1,1-dimethyl-3-nitratopropylamino)-2-propanol, hemi-fumarate, m.p. 119°–121°.
87. 1-p-Methoxyphenoxy-3-(1,1-dimethyl-3-nitratopropylamino)-2-propanol.
88. 1-o-Ethoxyphenoxy-3-(1,1-dimethyl-3-nitratopropylamino)-2-propanol.
89. 1-(p-2-Methoxyethylphenoxy)-3-(1,1-dimethyl-3-nitratopropylamino)-2-propanol.
90. 1-(p-2-Isopropoxyethoxymethylphenoxy)-3-(1,1-dimethyl-3-nitratopropylamino)-2-propanol.
91. 1-o-Methylthiophenoxy-3-(1,1-dimethyl-3-nitratopropylamino)-2-propanol.
92. 1-p-Methylthiophenoxy-3-(1,1-dimethyl-3-nitratopropylamino)-2-propanol.
93. 1-o-Vinylphenoxy-3-(1,1-dimethyl-3-nitratopropylamino)-2-propanol.
94. 1-o-Allylphenoxy-3-(1,1-dimethyl-3-nitratopropylamino)-2-propanol.
95. 1-p-Allylphenoxy-3-(1,1-dimethyl-3-nitratopropylamino)-2-propanol.
96. 1-p-Allyloxyphenoxy-3-(1,1-dimethyl-3-nitratopropylamino)-2-propanol.
97. 1-o-Propargylphenoxy-3-(1,1-dimethyl-3-nitratopropylamino)-2-propanol.
98. 1-p-Propargylphenoxy-3-(1,1-dimethyl-3-nitratopropylamino)-2-propanol.
99. 1-o-Propargyloxyphenoxy-3-(1,1-dimethyl-3-nitratopropylamino)-2-propanol.
100. 1-p-Propargyloxyphenoxy-3-(1,1-dimethyl-3-nitratopropylamino)-2-propanol.
101. 1-o-Cyclopropylphenoxy-3-(1,1-dimethyl-3-nitratopropylamino)-2-propanol.
102. 1-o-Cyclobutylphenoxy-3-(1,1-dimethyl-3-nitratopropylamino)-2-propanol.
103. 1-o-Cyclopentylphenoxy-3-(1,1-dimethyl-3-nitratopropylamino)-2-propanol.
104. 1-o-Cyclohexylphenoxy-3-(1,1dimethyl-3-nitratopropylamino)-2-propanol, hemi-fumarate, m.p. 125°–127°.
105. 1-o-Cycloheptylphenoxy-3-(1,1-dimethyl-3-nitratopropylamino)-2-propanol.
106. 1-o-Cyclooctylphenoxy-3-(1,1-dimethyl-3-nitratopropylamino)-2-propanol.
107. 1-o-Cyclopropyloxyphenoxy-3-(1,1-dimethyl-3-nitratopropylamino)-2-propanol.
108. 1-p-Cyclopropyloxyphenoxy-3-(1,1-dimethyl-3-nitratopropylamino)-2-propanol.
109. 1-o-Cyclobutyloxyphenoxy-3-(1,1-dimethyl-3-nitratopropylamino)-2-propanol.
110. 1-p-Cyclobutyloxyphenoxy-3-(1,1-dimethyl-3-nitratopropylamino)-2-propanol.
111. 1-o-Cyclopentyloxyphenoxy-3-(1,1-dimethyl-3-nitratopropylamino)-2-propanol.
112. 1-p-Cyclopentyloxyphenoxy-3-(1,1-dimethyl-3-nitratopropylamino)-2-propanol.
113. 1-o-Cyclohexyloxyphenoxy-3-(1,1-dimethyl-3-nitratopropylamino)-2-propanol.
114. 1-p-Cyclohexyloxyphenoxy-3-(1,1-dimethyl-3-nitratopropylamino)-2-propanol.
115. 1-o-Cycloheptyloxyphenoxy-3-(1,1-dimethyl-3-nitratopropylamino)-2-propanol.
116. 1-o-Cyclooctyloxyphenoxy-3-(1,1-dimethyl-3-nitratopropylamino)-2-propanol.
117. 1-(1-Naphthyloxy)-3-(1,1-dimethyl-3-nitratopropylamino)-2-propanol.
118. 1-(4-Indanyloxy)-3-(1,1-dimethyl-3-nitratopropylamino)-2-propanol.
119. 1-(4-Indenyloxy)-3-(1,1-dimethyl-3-nitratopropylamino)-2-propanol.
120. 1-(5-Tetralyloxy)-3-(1,1-dimethyl-3-nitratopropylamino)-2-propanol.
121. 1-(4-Indolyloxy)-3-(1,1-dimethyl-3-nitratopropylamino)-2-propanol.
122. 1-(2-Methyl-4-indolyloxy)-3-(1,1-dimethyl-3-nitratopropylamino)-2-propanol.
123. 1-(2,3-Dimethyl-4-indolyloxy)-3-(1,1-dimethyl-3-nitratopropylamino)-2-propanol.
124. 1-(4-Carbazolyloxy)-3-(1,1-dimethyl-3-nitratopropylamino)-2-propanol, m.p. 168°–170°.
125. 1-(1,2,3,4-Tetrahydro-2-oxo-5-quinolyloxy)-3-(1,1-dimethyl-3-nitratopropylamino)-2-propanol.
126. 1-o-Cyanophenoxy-3-(1,1,3-trimethyl-3-nitratopropylamino)-2-propanol, hemi-fumarate, m.p. 140°–142°.
127. 1-o-Isopropylphenoxy-3-(1,1,3-trimethyl-3-nitratopropylamino)-2-propanol.
128. 1-o-Methoxyphenoxy-3-(1,1,3-trimethyl-3-nitratopropylamino)-2-propanol, hemi-fumarate, m.p. 122°–123°.
129. 1-o-Allyloxyphenoxy-3-(1,1,3-trimethyl-3-nitratopropylamino)-2-propanol, hemi-fumarate, m.p. 97°–99°.
130. 1-(4-Indenyloxy)-3-(1,1,3-trimethyl-3-nitratopropylamino)-2-propanol.
131. 1-(4-Indolyloxy)-3-(1,1,3-trimethyl-3-nitratopropylamino)-2-propanol.
132. 1-(4-Carbazolyloxy)-3-(1,1,3-trimethyl-3-nitratopropylamino)-2-propanol.
133. 1-o-Cyanophenoxy-3-(1-methyl-4-nitratobutylamino)-2-propanol.
134. 1-o-Isopropylphenoxy-3-(1-methyl-4-nitratobutylamino)-2-propanol.
135. 1-o-Methoxyphenoxy-3-(1-methyl-4-nitratobutylamino)-2-propanol.
136. 1-o-Allyloxyphenoxy-3-(1-methyl-4-nitratobutylamino)-2-propanol.
137. 1-(4-Indenyloxy)-3-(1-methyl-4-nitratobutylamino)-2-propanol.
138. 1-(4-Indolyloxy)-3-(1-methyl-4-nitratobutylamino)-2-propanol.
139. 1-(4-Carbazolyloxy)-3-(1-methyl-4-nitratobutylamino)-2-propanol.
140. 1-o-Cyanophenoxy-3-(1,1-dimethyl-4-nitratobutylamino)-2-propanol.
141. 1-o-Isopropylphenoxy-3-(1,1-dimethyl-4-nitratobutylamino)-2-propanol.
142. 1-o-Methoxyphenoxy-3-(1,1-dimethyl-4-nitratobutylamino)-2-propanol.
143. 1-o-Allyloxyphenoxy-3-(1,1-dimethyl-4-nitratobutylamino)-2-propanol.
144. 1-(4-Indenyloxy)-3-(1,1-dimethyl-4-nitratobutylamino)-2-propanol.
145. 1-(4-Indolyloxy)-3-(1,1-dimethyl-4-nitratobutylamino)-2-propanol.
146. 1-(4-Carbazolyloxy)-3-(1,1-dimethyl-4-nitratobutylamino)-2-propanol.

Example 147

A mixture of 17.5 g of 1-o-cyanophenoxy-2,3-epoxypropane and 14.8 g of 1,1-dimethyl-3-nitratopropylamine in 45 ml of ethanol is left to stand at 20° for 15 hours. The mixture is evaporated; the residue is worked up in the customary manner; and there is produced 1-o-cyanophenoxy-3-(1,1-dimethyl-3-nitrato-propylamino)-2-propanol, m.p. 91°–94°.

EXAMPLE 148

A solution of 20.6 g of 1-o-allyloxyphenoxy-2,3-epoxypropane and 15 g of 1-methyl-3-nitratopropylamine in 200 ml of methanol is stirred at 25° for 60 hours and then evaporated. After customary working up, this yields 1-o-allyloxyphenoxy-2-(1-methyl-3-nitratopropylamino)-2-propanol. Hemi-fumarate, m.p. 100°–102°.

EXAMPLE 149

A mixture of 19.7 g of 1-o-methoxyphenoxy-3-amino-2-propanol (obtainable by reacting 1-o-methoxyphenoxy-2,3-epoxypropane with $NH_3$), 13.8 g of potassium carbonate, 22 g of 1-methyl-3-nitratopropyl bromide and 100 ml of tetrahydrofuran is boiled for 24 hours, while stirring. The mixture is filtered; the filtrate is evaporated; and the residue is worked up in the customary manner, yielding 1-o-methoxyphenoxy-3-(1-methyl-3-nitratopropylamino)-2-propanol, hemi-fumarate, m.p. 127°–128°.

EXAMPLE 150

A mixture of 13.3 g of 4-hydroxyindole, 22.7 g of 1-chloro-3-(1-methyl-3-nitratopropylamino)-2-propanol (obtainable from epichlorohydrin and 1-methyl-3-nitratopropylamine), 8 g of sodium hydroxide, 400 ml of ethanol and 20 ml of water is heated at 70° for 10 hours. The mixture is evaporated and the residue is worked up in the customary manner, yielding 1-(4-indolyloxy)-3-(1-methyl-3-nitratopropylamino)-2-propanol, m.p. 57°–60°.

EXAMPLE 151

10 g of N-[2-hydroxy-3-(p-2-isopropoxyethoxymethylphenoxy)-propyl]-N-(1-methyl-3-nitratopropyl)-acetamide [obtainable by reacting Na p-(2-isopropoxyethoxymethyl)-phenolate with N-(2-hydroxy-3-bromopropyl-N-(1-methyl-3-nitratopropyl)-acetamide] and 250 ml of 20% hydrochloric acid are warmed at 50° for 4 hours. The reaction mixture is evaporated and the residue is worked up in the customary manner, yielding 1-(p-2-isopropoxyethoxymethylphenoxy)-3-(1-methyl-3-nitratopropylamino)-2-propanol, hemi-fumarate, m.p. 90°–92°.

EXAMPLE 152

10 g of 1-o-methoxyphenoxy-2-acetoxy-3-(1-methyl-3-nitratopropylamino)-propane [obtainable from Na o-methoxyphenolate and 1-bromo-2-acetoxy-3-(1-methyl-3-nitratopropylamino)-propane] and 250 ml of 10% ethanolic NaOH are warmed at 50° for 2 hours. The reaction mixture is evaporated and the residue is worked up in the customary manner yielding 1-o-methoxyphenoxy-3-(1-methyl-3-nitratopropylamino)-2-propanol, hemi-fumarate, m.p. 127°–128°.

EXAMPLE 153

A mixture of 4.05 g of 1-(4-carbazolyloxy)-3-(1,1-dimethyl-3-bromopropylamino)-2-propanol, 2.8 g of mercury-I nitrate and 60 ml of 1,2-dimethoxyethane is warmed at 50° for 2 hours. After customary working up, this gives 1-(4-carbazolyloxy)-3-(1,1-dimethyl-3-nitratopropylamino)-2-propanol, m.p. 168°–170°.

The examples which follow relate to pharmaceutical formulations which contain amines of formula I or their acid addition salts:

EXAMPLE A: Tablets

A mixture of 1 kg of 1-o-allyloxy-phenoxy-3-(1-methyl-3-nitratopropylamino)-2-propanol hemi-fumarate, 4 kg of lactose, 1.2 kg of potato starch, 0.2 kg of talc and 0.1 kg of magnesium stearate is compressed into tablets in the customary manner, in such a way that each tablet contains 10 mg of active ingredient.

EXAMPLE B: Dragees

Tablets are pressed analogously to Example A and these are then coated in the customary manner with a coating of sucrose, potato starch, talc, tragacanth and dyestuff.

EXAMPLE C: Capsules 2 kg of 1-o-methoxy-phenoxy-3-(1,1-dimethyl-3-nitratopropylamino)-2-propanol hemi-fumarate are filled in the customary manner into hard gelatine capsules so that each capsule contains 20 mg of the active ingredient.

EXAMPLE D: Ampoules

A solution of 1 kg of 1-(4-indolyloxy)-3-(1-methyl-3-nitratopropylamino)-2-propanol in 30 l of twice distilled water is sterile-filtered, filled into ampoules, and lyophilized under sterile conditions and the ampoules are sealed under sterile conditions. Each ampoule contains 1 mg of active ingredient.

Tablets, dragees, capsules and ampoules which contain one or more of the other active compounds of formula I and/or their physiologically acceptable acid addition salts are obtainable analogously.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 1-aryloxy-3-nitratoalkylamino-2-propanol of the formula

Ar—O—CH$_2$—CHOH—CH$_2$—NH—R wherein
Ar is phenyl; phenyl substituted by (a) halogen, (b) cyano, (c) $C_{1-7}$ alkanoylamino, (d) benzoylamino, (e) alkanoyl of 1–4 carbon atoms, (f) $C_{1-10}$ alkyl, (g) $C_{1-10}$ alkoxy, $C_{1-10}$ alkoxy in which the carbon chain contains one ether oxygen atom, $C_{1-10}$ alkyl in which the carbon chain contains 1 or 2 ether oxygen atoms, $C_{1-10}$ alkylthio or $C_{1-10}$ alkyl in which the carbon chain contains one thioether sulfur atom, (h) $C_{1-10}$ alkenyl or $C_{1-10}$ alkynyl, (i) the residues (g) containing a double or triple bond, (j) cycloalkyl of 3–8 carbon atoms or (k) cycloalkoxy of 3–8 carbon atoms; naphthyl; indanyl; indenyl; 1,2,3,4-tetrahydronaphthyl; indolyl; indolyl substituted by alkyl of 1–4 carbon atoms; carbazolyl; or 1,2,3,4-tetrahydro-2-oxoquinolyl, and
R is nitratoalkyl of 2–10 carbon atoms,
and the physiologically acceptable acid addition salts thereof.

2. 1-o-Allyloxy-phenoxy-3-(1-methyl-3-nitratopropylamino)-2-propanol;
1-(1-naphthyloxy)-3-(1-methyl-3-nitratopropylamino)-2-propanol;
1-o-isopropylphenoxy-3-(1-methyl-3-nitratopropylamino)-2-propanol;
1-o-methoxyphenoxy-3-(1-methyl-3-nitratopropylamino)-2-propanol;
1-(4-indolyloxy)-3-(1-methyl-3-nitratopropylamino)-2-propanol;
1-o-cyanophenoxy-3-(1,1-dimethyl-3-nitratopropylamino)-2-propanol; or
1-(4-carbazolyloxy)-3-(1,1-dimethyl-3-nitratopropylamino)-2-propanol;

compounds of claim 1.

3. A compound of claim 1, wherein R is $-CZ^1Z^2-(CH_2)_m-CZ^3Z^4-O-NO_2$ wherein $Z^1$ to $Z^4$ are each H or $CH_3$ and m is 0–2.

4. A pharmaceutical composition comprising an amount of a compound of claim 1 effective as a β-receptor blocker and a pharmaceutically acceptable carrier.

5. A method of achieving blockage of β-receptors in mammals which comprises administering an amount of a compound of claim 1 effective as a β-receptor blocker.

6. 1-o-allyloxy-phenoxy-3-(1,1-dimethyl-3-nitratopropylamino)-2-propanol, a compound of claim 1.

* * * * *